(12) United States Patent
Suh et al.

(10) Patent No.: US 10,493,110 B2
(45) Date of Patent: Dec. 3, 2019

(54) HONEYBEE POLLEN COMPOSITION

(71) Applicant: NSB CO., LTD., Yeongcheon-si, Gyeongsangbuk-do (KR)

(72) Inventors: Hwa Jin Suh, Gunpo-si (KR); Se Gie Kim, Gyeongsan-si (KR); Yun Sik Choi, Seoul (KR); Il Kyung Chung, Daegu (KR)

(73) Assignee: NSB CO., LTD., Yeongcheon-si, Gyeongsangbuk-Do (KR)

( * ) Notice: Subject to any disclaimer, the term of this patent is extended or adjusted under 35 U.S.C. 154(b) by 200 days.

(21) Appl. No.: 15/743,095

(22) PCT Filed: Dec. 15, 2015

(86) PCT No.: PCT/KR2015/013694
§ 371 (c)(1),
(2) Date: Jan. 9, 2018

(87) PCT Pub. No.: WO2017/014375
PCT Pub. Date: Jan. 26, 2017

(65) Prior Publication Data
US 2019/0076483 A1 Mar. 14, 2019

(30) Foreign Application Priority Data
Jul. 22, 2015 (KR) ........................ 10-2015-0103720

(51) Int. Cl.
| | | |
|---|---|---|
| A61K 36/00 | (2006.01) | |
| A61K 35/644 | (2015.01) | |
| A61Q 19/00 | (2006.01) | |
| A61K 47/10 | (2017.01) | |
| A61K 47/38 | (2006.01) | |
| A61K 8/98 | (2006.01) | |

(52) U.S. Cl.
CPC ............ *A61K 35/644* (2013.01); *A61K 8/988* (2013.01); *A61K 47/10* (2013.01); *A61K 47/38* (2013.01); *A61Q 19/00* (2013.01)

(58) Field of Classification Search
CPC .................................................... A61K 36/00

USPC ......................................................... 424/725
See application file for complete search history.

(56) References Cited

FOREIGN PATENT DOCUMENTS

| CN | 104431678 A | 3/2015 |
|---|---|---|
| JP | 2007037529 A | 2/2007 |
| JP | 2010043015 A | 2/2010 |
| KR | 10-0894834 A | 4/2009 |
| KR | 10-1180909 A | 9/2012 |
| KR | 20140106990 A | 9/2014 |

OTHER PUBLICATIONS

International Search Report for International Application No. PCT/KR2015/013694 (2 Pages) (dated Apr. 28, 2016).
Komosinska-Vassev et al., "Bee Pollen: Chemical Composition and Therapeutic Application", Evidence-Based Complementary and Alternative Medicine, 2015, vol. 2015, No. 297425, pp. 1-6.

*Primary Examiner* — Michael V Meller
(74) *Attorney, Agent, or Firm* — Lucas & Mercanti, LLP

(57) ABSTRACT

The present invention relates to a honeybee pollen composition, and more particularly to a honeybee pollen composition prepared by mixing solidified honeybee pollen with distilled water and an admixture consisting of a dispersant, a preservative, a thickener, an antioxidant, or a neutralizer and then performing pulverization with a particle size of 100 to 500 nm, resulting in an efficient disruption of cell walls of the honeybee pollen and making the composition into a formulation available for easier ingestion in the body or skin, where the admixture, including a dispersant, a preservative, a thickener, an antioxidant, a neutralizer, etc., is added to the solidified honeybee pollen in the pulverization process to increase the stability, antioxidant effects and polyphenol content of the honeybee pollen composition, thereby acquiring availability of the composition as a cosmetic material or a pharmaceutical composition.

1 Claim, 10 Drawing Sheets

1st control group  2nd test group  3rd test group  4th test group
(stored in room temp.)

HONEYBEE POLLEN COMPOSITION

CROSS-REFERENCE TO RELATED APPLICATIONS

This application is a 371 of PCT/KR2015/013694, filed Dec. 15, 2015, which claims the benefit of KR 10-2015-0103720 filed Jul. 22, 2015, the contents of each of which are incorporated herein by reference.

TECHNICAL FIELD

The present invention relates to a honeybee pollen composition, and more particularly to a honeybee pollen composition prepared by mixing solidified honeybee pollen with distilled water and an admixture consisting of a dispersant, a preservative, a thickener, an antioxidant, or a neutralizer and then performing pulverization with a particle size of 100 to 500 nm, resulting in an efficient disruption of cell walls of the honeybee pollen and making the composition into a formulation available for easier ingestion in the body or skin, where the admixture including a dispersant, a preservative, a thickener, an antioxidant, a neutralizer, etc. is added to the solidified honeybee pollen in the pulverization process to increase the stability, antioxidant effects and polyphenol content of the honeybee pollen composition, thereby acquiring availability of the composition as a cosmetic material or a pharmaceutical composition.

BACKGROUND ART

Honeybee pollen, a material of royal jelly, is the pollen ball that has been carried by worker honeybees back to the hive in sacs on their legs and stored as a food for young bee. The pollen gathered from the flowers of plants and mixed with parotin and bee salivary secretions released from the mouthpart of honeybees is referred to as "honeybee pollen".

1 g of honeybee pollen contains two thousand to six hundred thousand pollen particles in combination with about two hundred other ingredients, including twelve of sixteen minerals essential to the human body. The honeybee pollen is loaded with more vitamin C than other foods. According to a report, 4.9 g of fiber is contained in 100 g of honeybee pollen. The composition of honeybee pollen according to the Korea Beekeeping Association is as presented in Table 1.

TABLE 1

| Ingredient | Types | Content |
| --- | --- | --- |
| Proteins | — | 23-25% |
| Carbohydrates | — | 25-27% |
| Minerals | 17 or more types | 2.5-3.0% |
| Amino acids | 18 or more types | High content of 10 amino acids in addition to 8 essential amino acids |
| Vitamins | 16 or more types | High content |
| Others | Enzymes, coenzymes, etc. | 20-25% |

According to the Korea Beekeeping Association, the honeybee pollen contains rutin (17 mg/g) making the blood vessels strong to strengthen the capillaries and about 5,000 enzymes boosting metabolism and digestive functions to enhance the condition of bodily strength and stamina and strengthen the physiological functions, thereby improving autotherapeutic abilities and immunity and helping prevent geriatric diseases and arteriosclerosis. Further, the honeybee pollen is rich in enzymes of all kinds and vitamin B, providing anti-aging functions, helping skin regeneration, and preventing skin aging. Containing a hormone called "gonadotropin" similar to the pituitary hormone, it activates the generative functions and makes curative effects against prostatitis and prostatism. Besides, the antianemic factor contained in the honeybee pollen causes a rapid increase in the number of red blood cells and hemoglobin to help the cure of anemia and also makes good effects in reducing the stress, improving neuropathy, promoting concentration and retentive memory, alleviating menopausal syndrome and premenstrual syndrome, increasing dietetic effects and a recovery from illness, preventing adult diseases, and enhancing digestive functions.

According to the results of studies in Europe, the honeybee pollen is very effective in improving the symptoms of benign prostatic hyperplasia (Buck et al., 1990, British Journal of Urology, Treatment of outflow tract obstruction due to benign prostatic hyperplasia with the pollen extract, cernilton. A double-blind, placebo-controlled study, 66(4), 398-404; Yasumoto et al., 1995, Clinical Therapeutics, Clinical evaluation of long-term treatment using cernitin pollen extract in patients with benign prostatic hyperplasia, 17(1), 82-87). Hence, the dried honeybee pollen is formulated in the form of pills and currently available for the cure of various prostatic diseases, but it has never been permissioned as a pharmaceutical substance. The honeybee pollen currently available is mostly used in the form of health supplements or food additives.

Korean Registration Patent No. 10-1180909 discloses a preparation method for a fermented honeybee pollen liquor with improved flavor and a fermented honeybee pollen liquor prepared by the method. The method of the cited patent includes the steps of performing pulverization of honeybee pollen into powder and then fermenting the honeybee pollen powder with either one strain of *Saccharomyces cerevisiae* or *Lactobacillus plantarum* and another strain, *Aspergillus niger*, to prepare a fermented honeybee pollen liquor with improved flavor and absorbable nutrients. Korean Registration Patent No. 10-0894834 is directed to a preparation method for fermented pollen, a fermented pollen prepared by the method, and a food including the fermented pollen. The method of the cited patent includes mixing pollen with at least one selected from the group consisting of a grain, a bean, and a rice bran, sterilizing and cooling the pollen mixture, and then inoculating filamentous fungi and bacteria into the pollen mixture to cause fermentation and prepare a fermented pollen. By the fermentation method, the outer covering of pollen is decomposed so that the active ingredients of pollen can be taken in the form of a food with efficiency.

The shell structure of honeybee pollen consists of an outer covering, exine, and an inner covering, intine. The exine is mostly hard to break down by animals, insects, strong acids, alkali, digestive enzymes, etc. (Brooks, Shaw 1997, Recent developments in the chemistry, biochemistry, geochemistry, and post-tetrad ontogeny of sporopollenins derived from pollen and spore exine. Heslop-Harrison, J(ed) pollen: development and physiology. Butterworths London. Pp. 99-114). Further, the honeybee pollen is not easy to break with satisfaction by pulverization using a ball mill or a hammer mill as well as a French presser, a Bantam mill, a glass bead mill, a homogenizer, or a sonicator (Bong-Woo, Lee, 1989. a study on the change of chemical ingredients in the processing of pollen loads. a master's thesis, Graduate school of food technology in Chung-Ang University). When taking honeybee pollen as a pharmaceutical composition, it is important to break the hard exine of the honeybee pollen so that the contents can be instantly subjected to the actions of digestive enzymes. In making the use of honeybee pollen in cosmetics, the physical disruption of exine and the development of appropriate formulations are particularly required.

In other words, there is an urgent demand for developing a method for preparing a honeybee pollen that involves preparing a honeybee pollen composition in the form of a formulation available for easier ingestion of the honeybee pollen in the body or skin by efficiently destroying the cell walls of the honeybee pollen rather than using fermentation with the aid of bacteria and fermenting agents added to the honeybee pollen.

PRIOR TECHNICAL DOCUMENTATIONS

Patent Documentations

KR Patent No. 10-1180909
KR Patent No. 10-0894834

DISCLOSURE OF INVENTION

The present invention is contrived to solve the above-described problems with the prior art and to provide necessary techniques. It is therefore an object of the present invention to provide a honeybee pollen composition prepared by mixing solidified honeybee pollen with distilled water and an admixture consisting of a dispersant, a preservative, a thickener, an antioxidant, or a neutralizer and then performing pulverization of the mixture so that the honeybee pollen composition has a particle size of 100 to 500 nm, resulting in an efficient disruption of cell walls of the honeybee pollen to make the composition into a formulation available for easier ingestion in the body or skin.

It is another object of the present invention to provide a honeybee pollen composition using an admixture, including a dispersant, a preservative, a thickener, an antioxidant, a neutralizer, etc., added to the solidified honeybee pollen in the pulverization process to increase the stability, antioxidant effects and polyphenol content of the honeybee pollen composition, thereby acquiring availability of the composition as a cosmetic material or a pharmaceutical composition.

In accordance with one embodiment of the present invention to achieve the objects, there is provided a honeybee pollen composition prepared by mixing 3 to 20 wt. % of solidified honeybee pollen, 0.1 to 4 wt. % of a dispersant, 0.1 to 4 wt. % of a preservative, 1 to 10 wt. % of a thickener, 0.05 to 0.3 wt. % of an antioxidant, 0.1 to 1 wt. % of a neutralizer, and distilled water for the rest, and then pulverizing the resultant mixture.

In the present invention, the dispersant is carboxymethyl cellulose; the preservative is 1,2-hexanediol; the thickener is carbopol; the antioxidant is sodium pyrosulfite; and the neutralizer is tetraethylammonium.

In the present invention, the honeybee pollen composition prepared by the pulverization process has a particle size of 100 to 500 nm.

EFFECTS OF THE INVENTION

The honeybee pollen composition in accordance with one embodiment of the present invention is prepared by mixing solidified honeybee pollen with distilled water and an admixture consisting of a dispersant, a preservative, a thickener, an antioxidant, or a neutralizer and then performing pulverization with a particle size of 100 to 500 nm, efficiently destroying the cell walls of the honeybee pollen to advantageously make the honeybee pollen composition into a formulation available for easier ingestion in the body or skin.

Namely, the honeybee pollen composition is prepared into a formulation available for the easier ingestion of the honeybee pollen in the body or skin by effective disruption of the cell walls of the honeybee pollen rather than fermentation activated with the aid of bacteria and fermenting agents added to the honeybee pollen. This method can simplify the process of preparing a honeybee pollen composition in the form of a formulation easily absorbed into the body or skin. It also prevents, to the maximum, a loss of active ingredients included in the honeybee pollen that may occur in the fermentation using bacteria added to the honeybee pollen.

In addition, the honeybee pollen composition according to one embodiment of the present invention uses an admixture, including a dispersant, a preservative, a thickener, an antioxidant, a neutralizer, etc., added to the solidified honeybee pollen in the pulverization process, which increases the stability, antioxidant effects and polyphenol content of the honeybee pollen composition and thereby acquires availability of the composition as a cosmetic material or a pharmaceutical composition.

BRIEF DESCRIPTIONS OF DRAWINGS

BEST MODES FOR CARRYING OUT THE INVENTION

Figure 1:
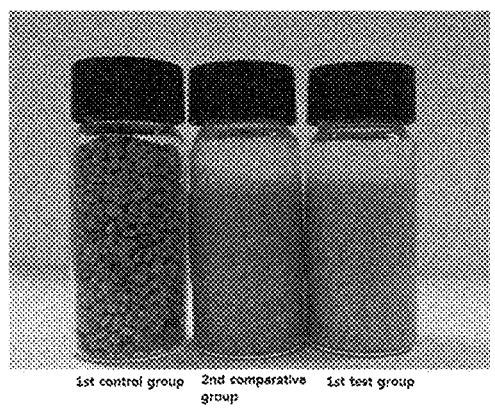
FIG. 1 is a photographic image showing a comparison of the formulations of the individual samples prepared from first and second comparative groups and a first test group immediately after the preparation.

Hereinafter, the present invention will be described in detail with reference to the following examples, which are given for the illustrations of the present invention only and not construed to limit the scope of the present invention. The examples of the present invention are subjected to various changes and modification and provided for those skilled in the art to understand the prevent invention more completely.

Throughout this specification, it will also be understood that the terms "comprises" and/or "comprising" specify the presence of the stated component but do not preclude the presence or addition of one or more other components.

The term "about or approximately" or "substantially" as used throughout this specification are intended to have meanings close to numerical values or ranges specified with an allowable error and intended to prevent accurate or absolute numerical values disclosed for the understanding of the present invention from being illegally or unfairly used any unconscionable third party. Through the specification, the term "step of" does not mean "step for".

Hereinafter, detailed description will be given as to a preparation method for a honeybee pollen composition and a honeybee pollen composition prepared by the method according to one embodiment of the present invention with reference to the componential analyses and activity tests. The honeybee pollen composition according to one embodiment of the present invention can be more definitely understood from the results of the after-mentioned componential analyses and activity tests.

The honeybee pollen composition according to one embodiment of the present invention is prepared by mixing solidified honeybee pollen with a dispersant, a preservative, a thickener, an antioxidant, and a neutralizer, adding distilled water, and then pulverizing the resultant mixture. This process is to improve the stability of the final honeybee pollen composition.

In accordance with one embodiment of the present invention, the pulverization process performed to prepare a honeybee pollen composition involves performing pulverization of a mixture composed of 3 to 20 wt. % of solidified honeybee pollen, 0.1 to 4 wt. % of a dispersant, 0.1 to 4 wt. % of a preservative, 1 to 10 wt. % of a thickener, 0.05 to 0.3 wt. % of an antioxidant, 0.1 to 1 wt. % of a neutralizer, and distilled water for the rest.

In accordance with one embodiment of the present invention, the dispersant is carboxymethyl cellulose; the preservative is 1,2-hexanediol; the thickener is carbopol; the antioxidant is sodium pyrosulfite; and the neutralizer is tetraethylammonium.

Carboxymethyl cellulose (CMC) is a substance prepared by reacting cellulose dissolved in an alkali with sodium monochloroacetate. If 40% or more of the hydroxyl groups in cellulose are carboxymethylated, the CMC is very soluble in cold water to form a stable colloidal solution with high viscosity. It is also edible. When a dispersant like carboxymethyl cellulose (CMC) is added in an amount of less than 0.1 wt. % with respect to the total weight percent of the honeybee pollen composition, it may deteriorate the dispersion of the honeybee pollen composition. When a dispersant is added in an amount of greater than 4 wt. % with respect to the total weight percent of the honeybee pollen composition, the content of the honeybee pollen is relatively reduced to make the honeybee pollen composition deficient in the active ingredients of the honeybee pollen.

1,2-hexanediol is a preservative used in cosmetic materials. When a preservative like 1,2-hexanediol is added in an amount of less than 0.1 wt. % with respect to the total weight percent of the honeybee pollen composition, it may cause deterioration in the preservative effectiveness. When a preservative is added in an amount of greater than 4 wt. % with respect to the total weight percent of the honeybee pollen composition, it increases the preservative effectiveness and relatively reduces the content of the honeybee pollen in the honeybee pollen composition to render the honeybee pollen composition deficient in the active ingredients of the honeybee pollen.

Carbopol is used as a material in clear gel-like emulsified products to increase the viscosity. When a thickener like Carbopol is added in an amount of less than 1 wt. % with respect to the total weight percent of the honeybee pollen composition, it is unable to increase the viscosity of the final honeybee pollen composition. When a thickener is added in an amount of greater than 10 wt. % with respect to the total weight percent of the honeybee pollen composition, it raises the viscosity of the honeybee pollen composition too high and relatively reduces the content of the honeybee pollen in the composition, making the honeybee pollen composition deficient in the active ingredients of the honeybee pollen.

Sodium pyrosulfite ($Na_2S_2O_5$) is a crystalline substance obtained by saturating an aqueous solution of sodium carbonate with sulfur dioxide for a long time and then evaporating the solution over highly concentrated sulfuric acid. This substance makes an antioxidant effect. When such an antioxidant as sodium pyrosulfite is added in an amount of less than 0.05 wt. % with respect to the total weight percent of the honeybee pollen composition, it results in an extremely low proportion of the antioxidant like sodium pyrosulfite so that the final honeybee pollen composition is oxidized and rendered not appropriate for foods, cosmetics, or pharmaceutical compositions. When an antioxidant is added in an amount of greater than 0.3 wt. % with respect to the total weight percent of the honeybee pollen composition, it relatively reduces the content of the honeybee pollen in the composition to make the honeybee pollen composition deficient in the active ingredients of the honeybee pollen.

Teteraethylammonium (TEA) is an alkaline material and, if used in combination with carbopol, plays an important role in increasing the viscosity of carbopol. When a neutralizer like tetraethylammonium (TEA) is added in an amount of less than 0.1 wt. % with respect to the total weight percent of the honeybee pollen composition, it results in an extremely low proportion of the neutralizer like TEA so that the neutralizer is unable to help increase the viscosity of carbopol. When a neutralizer is added in an amount of greater than 1 wt. % with respect to the total weight percent of the honeybee pollen composition, it may cause the ophthalmologic diseases or skin dryness as a side effect of TEA to make the honeybee pollen composition not appropriate for foods, cosmetics, or pharmaceutical compositions.

It is therefore most preferable to prepare a honeybee pollen composition by making a mixture composed of 3 to 20 wt. % of solidified honeybee pollen, 0.1 to 4 wt. % of a dispersant, 0.1 to 4 wt. % of a preservative, 1 to 10 wt. % of a thickener, 0.05 to 0.3 wt. % of an antioxidant, 0.1 to 1 wt. % of a neutralizer, and distilled water for the rest, and then pulverizing the mixture.

In a method according to one embodiment of the present invention, the honeybee pollen composition prepared by mixing solidified honeybee pollen with a dispersant, a preservative, a thickener, an antioxidant, a neutralizer, and distilled water and then pulverizing the mixture has a particle size of 100 to 500 nm as a result of the pulverization. The particle size range as defined above is determined from the results of an observational test on the exine of honeybee pollen according to the varied pulverization time in Example 1, which presents an experiment to observe the exine of honeybee pollen after pulverization according to the particle size of the pulverized composition. According to the observational test, only a few cell wall debris is seen in the extraction containing dispersed particles of honeybee pollen pulverized with a particle size of 500 nm (D of FIG. 5); on the contrary, there is no cell wall debris in the extraction containing dispersed particles of honeybee pollen pulverized with a particle size of 400 nm (E and F of FIG. 5).

In accordance with the morphological examination of honeybee pollen, it is most preferred to pulverize the honeybee pollen composition with a particle size of 100 to 500 nm in the pulverization process for preparation of the honeybee pollen composition for the sake of increasing the extraction efficiency for active ingredients from the honeybee pollen as a material for foods, cosmetics or pharmaceutical compositions.

Example 1

The change in formulation of honeybee pollen compositions prepared differently with varied conditions of the pulverization process for solidified honeybee pollen was examined to evaluate the degree of dispersion and stability. Then, an observational test was carried out to evaluate the pulverization of the pollen exine depending on the particle size of the honeybee pollen composition after the pulverization process. This procedure allowed it to determine the particle size of the honeybee pollen composition most ideal to enhance the extraction efficiency for active ingredients from the honeybee pollen used as a material for foods, cosmetics or pharmaceutical compositions.

1. Determination of Control and Test Groups

In order to determine the optimal particle size of the honeybee pollen composition, an observational test was performed to evaluate the change in formulation according to the pulverization time. In the test, the control groups were the solidified honeybee pollen and the test groups were prepared differently by varying the proportion of the sample added in the pulverization process. The descriptions of the control and test groups are presented in Tables 2 and 3, respectively. Carboxymethyl cellulose was used as a dispersant, 1,2-hexanediol as a preservative, Carbopol as a thickener, sodium pyrosulfite as an antioxidant, etraethylammonium as a neutralizer.

TABLE 2

| Control group | |
| --- | --- |
| $1^{st}$ control group | Solidified honeybee pollen |
| $2^{nd}$ control group | Solidified honeybee pollen pulverized with a particle size of 100 nm or above and then mixed with distilled water (5% of honeybee pollen and 95% of distilled water) |

The control and test groups were provided according to Tables 2 and 3, and the samples were prepared from the first and second control groups and the first test group. The first control group was the solidified honeybee pollen as it was; the second control group was the solidified honeybee pollen pulverized with a particle size of 1,000 nm or greater and mixed with distilled water; and the first test group was prepared by adding distilled water to the solidified honeybee pollen and pulverizing with a particle size of about 100 to 800 nm using a wet pulverizer. A comparison of the samples was made in regards to the formulation immediately after the completion of preparation. The results are shown in FIG. 1.

2. Observational Test on Change in Formulation of Honeybee Pollen Composition without an Admixture In the preparation of the samples corresponding to the first test group, the pulverization process was performed for different times; 1 hour, 2 hours, 3 hours, 4 hours, and five hours. The five different samples prepared from the first test group and the sample from the first control group were left at the room temperature of 25 to 35° C. for one week and then examined in regards to the change in formulation. The results are presented in FIG. 2.

Figure 2:
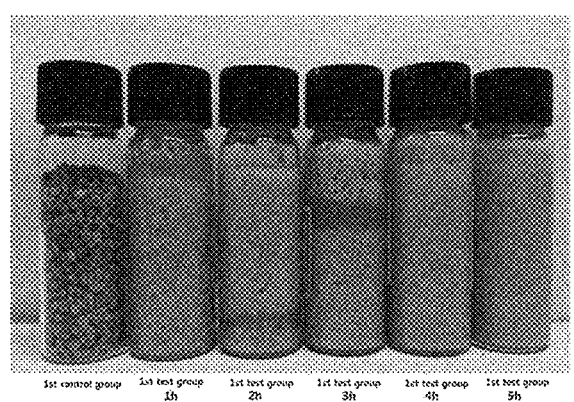
FIG. 2 is a photographic image showing the results of an observational test concerning the change in formulation of honeybee pollen compositions prepared without using an admixture.

As shown in FIG. 2, the five samples of the first test group prepared by pulverizing for different times of one to five hours without an admixture like a dispersant or a preservative in contrast to the control group of the solidified honeybee pollen and left at the room temperature of 25 to 35° C. for one week were all naturally fermented and thus rendered not available for foods, cosmetics, or pharmaceutical preparations.

When the exine is extracted effectively from the honeybee pollen, the active ingredients contained in the cells of the honeybee pollen provide environments preferable for the inhabitation of microorganisms to incur fermentation of the honeybee pollen composition during the one-month storage in the air or even at low temperatures. The fermented composition may cause denaturation of the ingredients inherently contained in the honeybee pollen or deteriorate in stability, so it is not available for foods, cosmetics, or pharmaceutical compositions.

A visual examination concerning the change in formulation after seven days revealed that the five samples of the first test group had fermentation. As can be seen from the results of the examination, the pulverization process performed for 1 to 5 hours resulted in a removal of the exine from the honeybee pollen, increasing the extraction efficiency for the active ingredients from the honeybee pollen, but also causing denaturation during the storage to deteriorate stability.

TABLE 3

| | Test group* | | | | | | |
| --- | --- | --- | --- | --- | --- | --- | --- |
| | $1^{st}$ | $2^{nd}$ | $3^{rd}$ | $4^{th}$ | $5^{th}$ | $6^{th}$ | $7^{th}$ |
| Honeybee pollen (wt. %) | 5 | 5 | 10 | 15 | 5 | 10 | 15 |
| Dispersant (wt. %) | — | 0.5 | 0.5 | 0.5 | 0.5 | 0.5 | 0.5 |
| Preservative (wt. %) | — | 0.4 | 0.4 | 0.4 | 0.4 | 0.4 | 0.4 |
| Thickener (wt. %) | — | — | — | — | 5 | 5 | 5 |
| Antioxidant (wt. %) | — | — | — | — | 0.075 | 0.075 | 0.075 |
| Neutralizer (wt. %) | — | — | — | — | 0.2 | 0.2 | 0.2 |
| Distilled water (wt. %) | 95.0% | 94.1% | 89.1% | 84.1% | 88.8% | 83.8% | 78.8% |

*Prepared by adding an admixture and distilled water to the solidified honeybee pollen and then pulverizing with a particle size of about 100 to 800 nm using a wet pulverizer.

3. Observational Test on Change in Formulation of Honeybee Pollen Composition with an Admixture In the preparation of honeybee pollen compositions, a dispersant and a preservative were added, but the portion (wt. %) of the honeybee pollen was varied. The samples thus obtained from the second, third and fourth test groups with a varied portion (wt. %) of the honeybee pollen and the sample from the first control group were kept at the room temperature of 25 to 35° C. for 3 months and then examined in regards to the change in formulation. The results are presented in FIG. 3.

Figure 3:
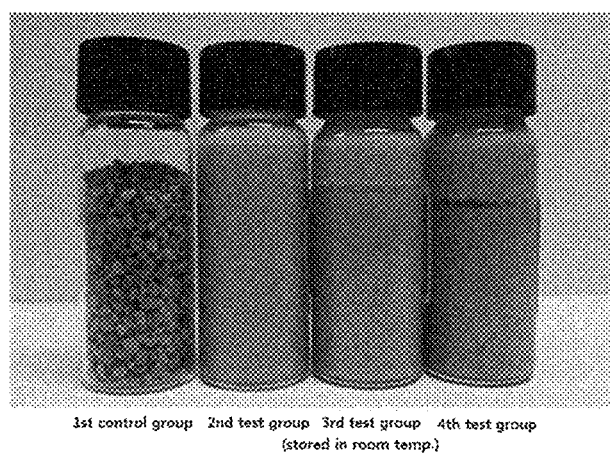
FIG. 3 is a photographic image showing the results of an observational test concerning the change in formulation of honeybee pollen compositions using an admixture.

As shown in FIG. 3, in all the samples of the second test group containing 5 wt. % of honeybee pollen, the third test group containing 10 wt. % of honeybee pollen and the fourth test group containing 15 wt. % of honeybee pollen as prepared using a dispersant and a preservative in the pulverization process, the pollen particles were maintained in dispersion on the water, as they were lighter than water, throughout the three-month storage at the room temperature. Unlike the sample of the first test group not treated with a dispersant or a preservative, these samples were not susceptible to fermentation, but acquired stability.

4. Observational Test on Change in Formulation of Honeybee Pollen Composition with an Admixture after an Accelerated Test In the preparation of honeybee pollen compositions, a dispersant, a preservative, a thickener, an antioxidant, and a neutralizer were added, but the portion (wt. %) of honeybee pollen was varied. The samples thus obtained from the fifth, sixth, and seventh test groups with a varied portion (wt. %) of honeybee pollen and the sample from the first control group were all subjected to an accelerated test at the temperature of about 48° C. for 30 days. The results are presented in FIG. 4.

Figure 4:
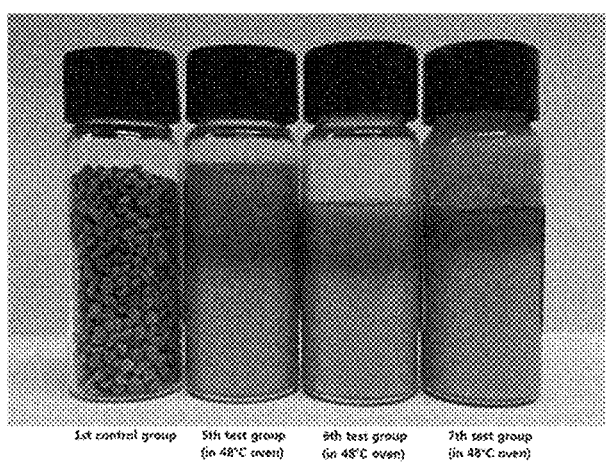
FIG. 4 is a photographic image showing the results of an observational test concerning the change in formulation of honeybee pollen compositions using an admixture after an accelerated test.

As shown in FIG. 4, the dispersion was stable due to the presence of admixtures in all the samples of the first test group containing 5 wt. % of honeybee pollen, the sixth test group containing 10 wt. % of honeybee pollen and the seventh test group containing 15 wt. % of honeybee pollen, which were all prepared using a dispersant, a preservative, a thickener, an antioxidant, and a neutralizer as admixtures in the pulverization process. From this fact, it is predictable that the formulations of the present invention are available for use with a stable structure at the room temperature for at least one year. It is based on the standards that a general cosmetic material is considered available for use at room temperature for one year when a visual examination concerning the formulation and dispersion stability recognizes no separation of layer in the cosmetic material left at about 45° C. for one month in an accelerated test. It is thus predictable that the samples of the fifth, sixth and seventh test groups according to one embodiment of the present invention are available for use with a stable structure at room temperature for at least one year.

Figure 6:
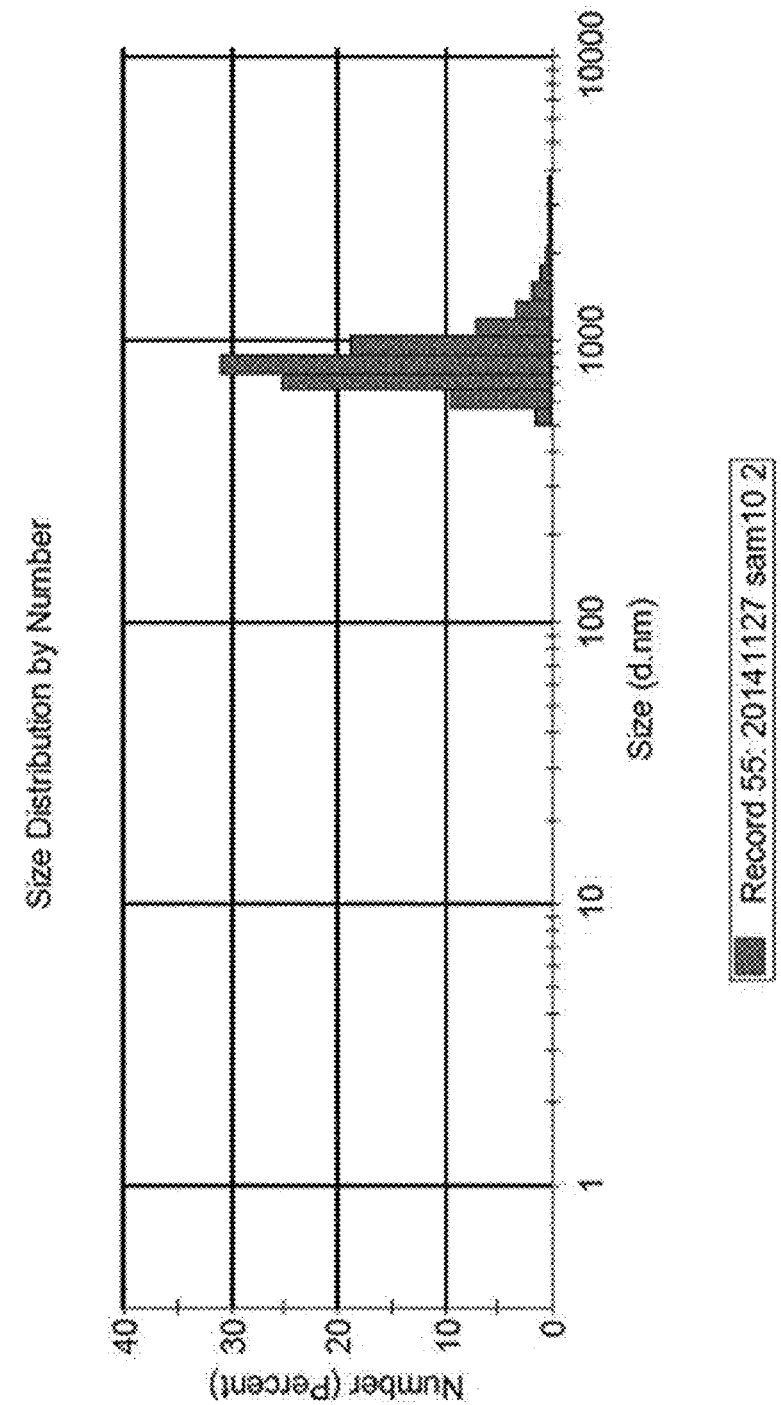
FIG. 6 is a graph showing the particle size of the honeybee pollen composition prepared by one-hour pulverization.
Figure 7:
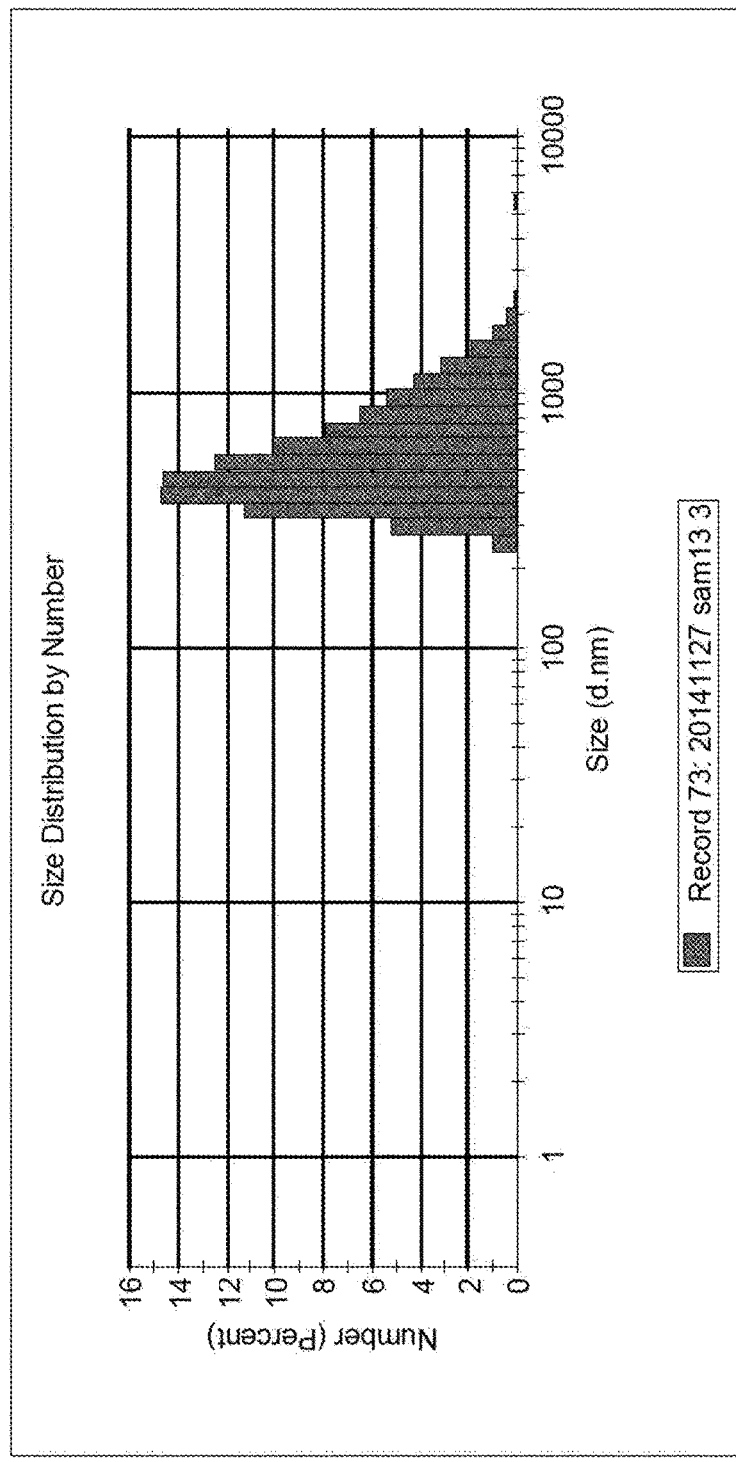
FIG. 7 is a graph showing the particle size of the honeybee pollen composition prepared by two-hour pulverization.
Figure 8:
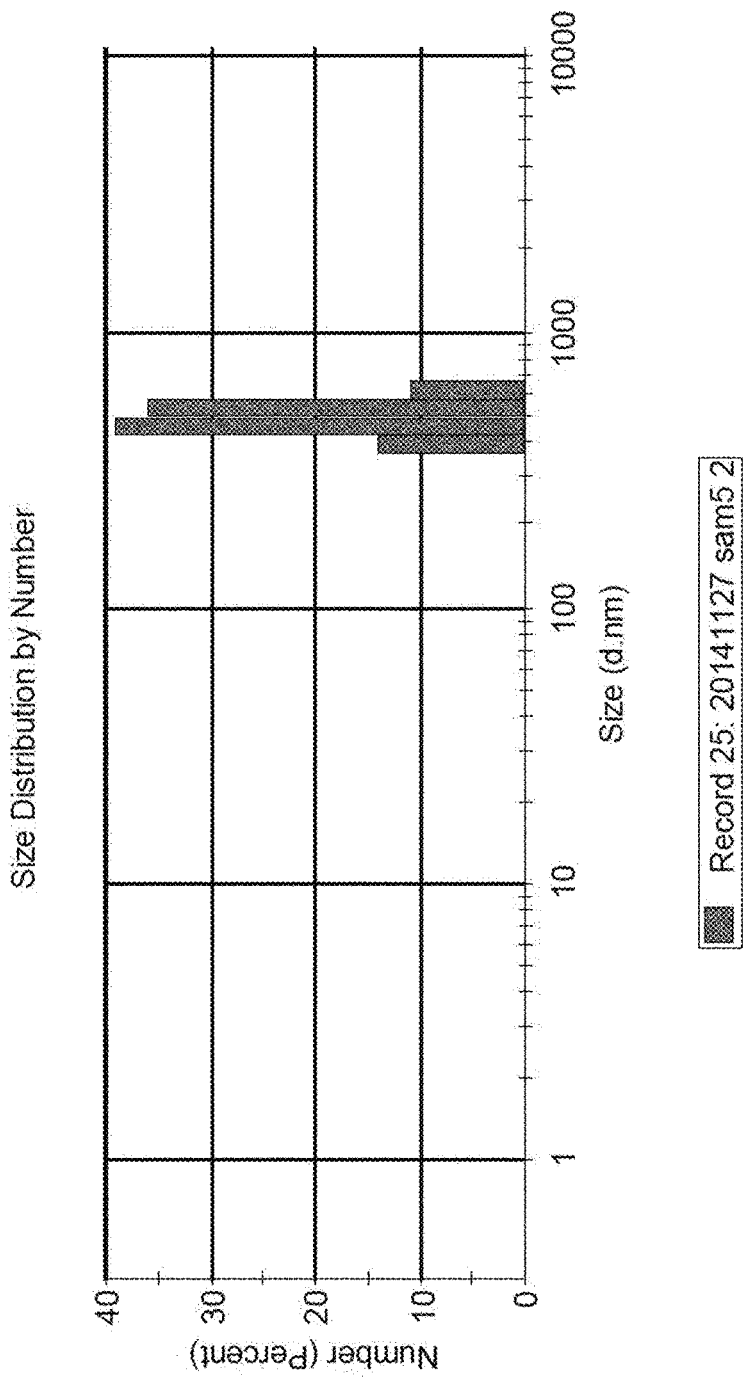
FIG. 8 is a graph showing the particle size of the honeybee pollen composition prepared by three-hour pulverization.
Figure 9:
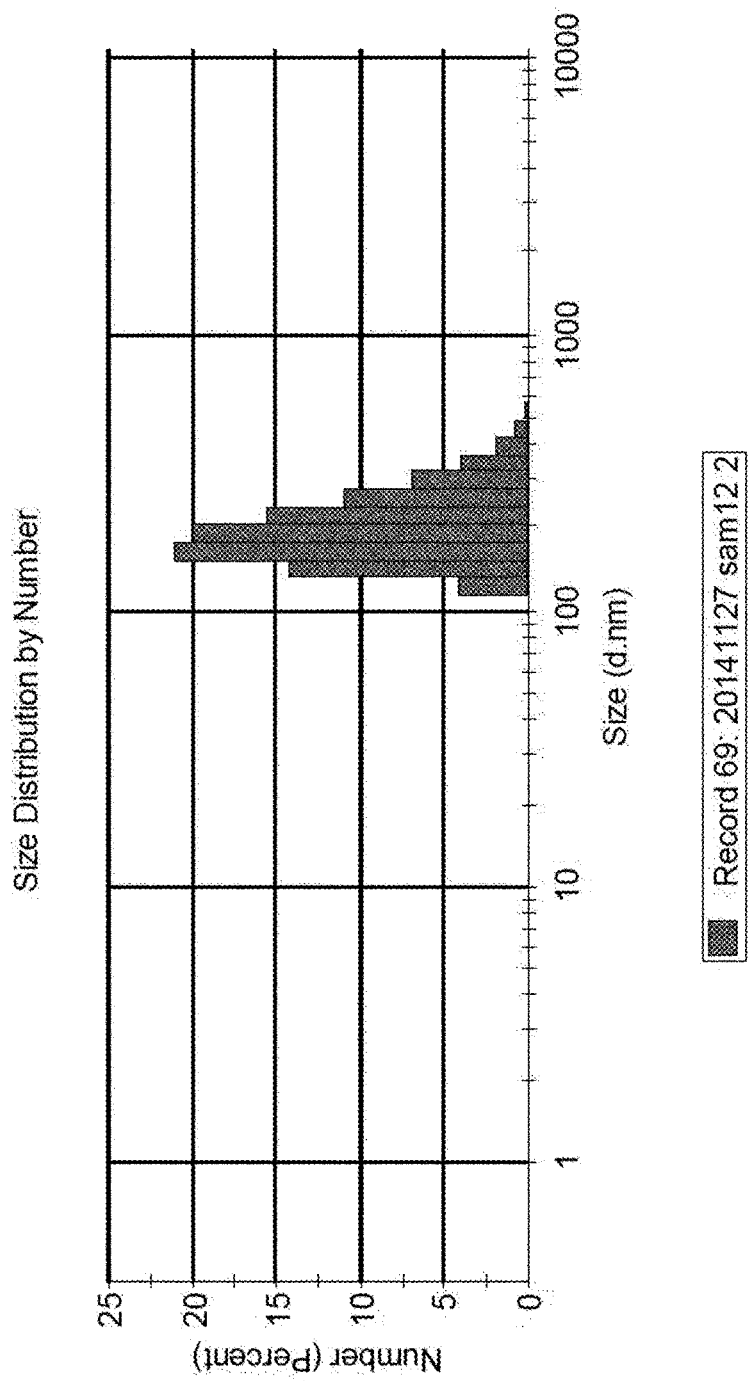
FIG. 9 is a graph showing the particle size of the honeybee pollen composition prepared by five-hour pulverization.

5. Observational Test after Pulverization of Pollen Exine Depending on the Pulverization Time In accordance with one embodiment of the present invention, solidified honeybee pollen was mixed with an admixture and distilled water and then pulverized to prepare a honeybee pollen composition. The honeybee pollen composition was measured in regards to the particle size depending on the pulverization time, and the pollen exine after pulverization was examined as a function of the particle size of the honeybee pollen composition. In other words, the morphology of the honeybee pollen was evaluated to determine the particle size of the honeybee pollen composition most ideal to raise the extraction efficiency for active ingredients from the honeybee pollen used as a material for foods, cosmetics, or pharmaceutical compositions. The results of examination on the pulverized pollen exine are presented in FIG. 5. Further, the measurement results in regards to the particle size of the samples prepared with a varied pulverization time are presented in FIG. 6 (one-hour pulverization), FIG. 7 (two-hour pulverization), FIG. 8 (three-hour pulverization), and FIG. 9 (four-hour pulverization).

Figure 5:
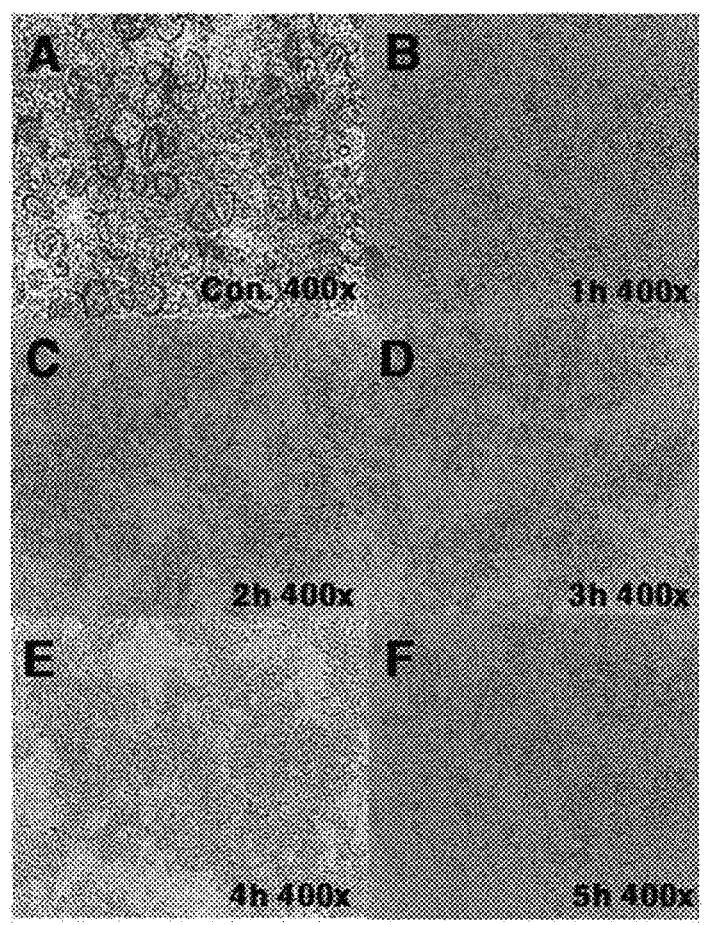
FIG. 5 is a photographic image showing the results of pulverization of pollen exine depending on the particle size of the honeybee pollen composition prepared by pulverization

As shown in FIG. 5, the samples prepared from the seventh test group by pulverization with a varied pulverization time of one hour, 2 hours, 3 hours, or 5 hours and the sample from the first control group defined as the solidified honeybee pollen by 30-minute pulverization with a homogenizer were all subjected to an optical microscopic examination with a magnification of 400×. From the examination, unbroken cell walls were found in a large amount of honeybee pollen in the sample of the first control group prepared by 30-minute pulverization with a homogenizer (A of FIG. 5).

In the examination of the samples prepared from the seventh test group with a varied pulverization time according to one embodiment of the present invention, only a few cell wall debris of honeybee pollen was seen in the extraction of the dispersed particles after the pulverization with a particle size of 500 nm to break the cell walls, which particle size was dependent upon the pulverization time (D of FIG. 5); but, there was no cell wall debris of honeybee pollen in the extraction of dispersed particles having a particle size of 100 to 400 nm (E and F of FIG. 5).

As can be seen from the morphological evaluation of the honeybee pollen according to the above-stated experiment, it is desirable to pulverize the honeybee pollen composition with a particle size of 100 to 500 nm in the pulverization process in order to enhance the extraction efficiency for active ingredients from the honeybee pollen used as a material for foods, cosmetics, or pharmaceutical compositions.

Example 2

A testing for evaluating the antioxidant activity was performed for a sample prepared from the first control group defined as the solidified honeybee pollen by 30 minutes of pulverization with a homogenizer and a sample of the honeybee pollen composition prepared from the seventh test group by 3 hours of pulverization.

For the evaluation of antioxidant activity, the ABTS radial scavenging activity and the DPPH radial scavenging activity were measured and assayed.

1. Measurement of ABTS Radical Scavenging Activity 7 mM ABTS (2,2'-azino-bis(3-ethylbenzothiazoline-6-sulphonic acid) buffer and 2.45 mM potassium persulfate ($K_2S_2O_8$) buffer were prepared and mixed at a volume ratio of 2:1 (ABTS buffer to potassium persulfate buffer) to prepare a stock buffer. The stock buffer was allowed to react for 12 to 16 hours in the dark. The buffer was then diluted to obtain an absorbance (O.D.) of about 0.7 at 734 nm. 0.1 ml of each sample prepared from the first control group or the seventh test group and diluted by concentration was added to 0.1 ml of the stock buffer. The reaction mixture was left at the room temperature for 6 minutes and moved to a 96-well plate. The absorbance of the mixture was taken at 734 nm and compared with the half maximal inhibitory concentration ($IC_{50}$) of each sample, where the $IC_{50}$ was the concentration of an inhibitor required to reduce the activity of radicals by half. The percentage inhibition was calculated according to the following Equation 1 (Nitaya Meenakshi R and Suganthi R, Int J Pharm Bio Sci 2013 April; 4(2): (B) 312-318) to determine the ABTS radical scavenging activity.

$$\text{Percentage Inhibition (\%)} = \frac{\text{Absorbance (O.D.) of control} - \text{Absorbance (O.D.) of sample}}{\text{Absorbance (O.D.) of control}} \quad \text{[Equation 1]}$$

The ABTS radical scavenging assay was performed as an evaluation of antioxidant activity for a sample prepared from the first control group defined as the solidified honeybee pollen by 30-minute pulverization with a homogenizer and a sample of the honeybee pollen composition prepared from the seventh test group by three-hour pulverization. According to the ABTS radical scavenging assay, the sample of crystalline honeybee pollen prepared without pulverization in accordance with one embodiment of the present invention had an $IC_{50}$ value of 217 µg/ml, whereas the sample prepared by the three-hour pulverization had a far lower $IC_{50}$ value of 32 µg/ml. This shows that the sample of a honeybee pollen composition prepared from the seventh test group containing 15 wt. % of honeybee pollen with respect to the total weight of the composition by three-hour pulverization had an antioxidant activity about 6.5 times higher. As a result, the pulverization process for removing the exine of honeybee pollen helps prevent the chemical denaturation of active ingredients contained in the cells of the honeybee pollen possibly occurring in the existing extraction method of pyrolysis, enzymatic extraction, etc. and allows the extraction of the active ingredients with stability, making it possible to obtain highly functional substances from the honeybee pollen.

2. Measurement of DPPH Radical Scavenging Activity

A working solution was prepared by mixing a DPPH (1,1-diphenyl-2-picrylhydrazyl) solution with a sample or a reference material according to Table 4. The reaction mixture was vortexed thoroughly and left at the room temperature for 5 minutes of reaction. The absorbance of the mixture was measured at 517 nm. The percentage inhibition was calculated according to the following Equation 2 (Nitaya Meenakshi R and Suganthi R, Int J Pharm Bio Sci 2013 April; 4(2): (B) 312-318).

TABLE 4

|   | DPPH solution | Sample | MeOH | Sample-dissolved solution |
|---|---|---|---|---|
| A | 0.1 ml | 0.1 ml | 0.8 ml | — |
| B | — | 0.1 ml | 0.9 ml | — |
| C | 0.1 ml | — | 0.8 ml | 0.1 ml |
| D | — | — | 0.9 ml | 0.1 ml |

$$\text{Percentage Inhibition (\%)} = \frac{(C-D)-(A-B)}{(C-D)} \times 100 \quad \text{[Equation 1]}$$

The DPPH radical scavenging assay was performed as an evaluation of antioxidant activity for a sample prepared from the first control group defined as the solidified honeybee pollen by 30-minute pulverization with a homogenizer and a sample of the honeybee pollen composition prepared from the seventh test group by three-hour pulverization. According to the DPPH radical scavenging assay, the sample of crystalline honeybee pollen prepared without pulverization in accordance with one embodiment of the present invention had an $IC_{50}$ value of 242.9 µg/ml, whereas the sample prepared by 3-hour pulverization had a far lower $IC_{50}$ value of 74.9 µg/ml. This shows that the sample of a honeybee pollen composition prepared from the seventh test group containing 15 wt. % of honeybee pollen with respect to the total weight of the composition by 3-hour pulverization had an antioxidant activity about 3.3 times higher. As a result, the pulverization process for removing the exine of honeybee pollen helps prevent the chemical denaturation of active ingredients contained in the cells of the honeybee pollen possibly occurring in the existing extraction method of pyrolysis, enzymatic extraction, etc. and allows the extraction of the active ingredients with stability, making it possible to obtain highly functional substances from the honeybee pollen.

Example 3

A testing for evaluating the polyphenol content was performed for a sample prepared from the first control group defined as the solidified honeybee pollen by 30 minutes of pulverization with a homogenizer and a sample of the honeybee pollen composition prepared from the seventh test group by 3 hours of pulverization. The evaluation results are presented in Table 5 and FIG. 10.

For the total phenolic concentration (TPC) assay, the quantity of polyphenol was determined according to the A.O.A.C method. Briefly, 3 ml of a 100-fold diluted sample solution was mixed thoroughly with 1 ml of Folin-Ciocalteu phenol reagent, followed by the addition of 0.2 ml of 1N HCl and 1 ml of saturated $Na_2CO_3$ solution. The mixture was left at the room temperature for one hour. The absorbance of the mixture was measured at 640 nm. The polyphenol content was calculated from a standard curve prepared with gallic (tannic) acid used as a reference material through the comparison of absorbance between the mixture and the reference material (Claudia Anesini, Graciela E. Ferrara, Rosana Filipi, J. Agric. Food Chem. 2008, 56, 9225-9229).

Figure 10:
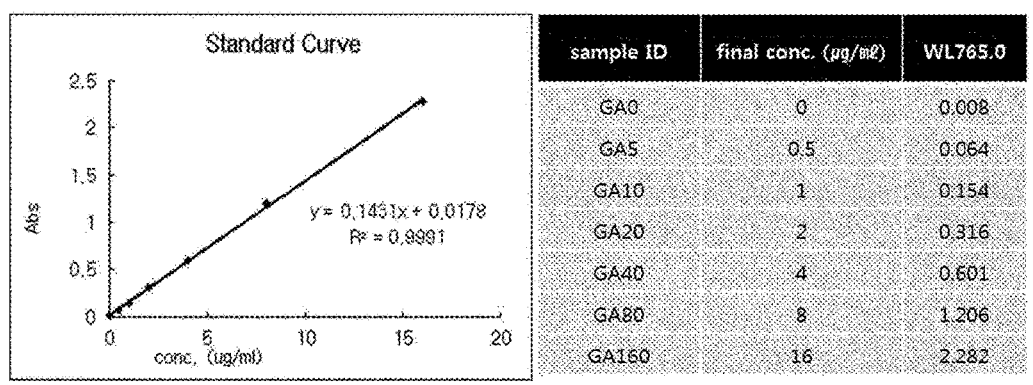
FIG. 10 is a standard curve showing the results of a total polyphenolic content (TPC) assay using gallic (tannic) acid as a reference substance.

The following Table 5 presents the results of a comparative analysis for the polyphenol content of a sample prepared from the first control group defined as the solidified honeybee pollen by 30-minute pulverization with a homogenizer and a sample of the honeybee pollen composition prepared from the seventh test group by 3-hour pulverization. FIG. 10 shows a standard curve prepared with gallic (tannic) acid used as a reference material.

TABLE 5

|   | $1^{st}$ test | $2^{nd}$ test | $3^{rd}$ test | Average (mg GA/mg ext) | Deviation |
|---|---|---|---|---|---|
| A | 0.011 | 0.010 | 0.010 | 0.010 | 0.000 |
| B | 0.118 | 0.121 | 0.118 | 0.119 | 0.001 |

(Average: total phenolic concentration (TPC) per 1 mg of honeybee pollen)

Table 5 shows the analytical results for the polyphenol content of a sample (A of Table 4) prepared from the first control group defined as the solidified honeybee pollen by 30-minute pulverization with a homogenizer and a sample (B of Table 4) of the honeybee pollen composition prepared from the seventh test group by 3-hour pulverization. According to the results of a comparative analysis for the polyphenol content, the sample (B of Table 4) prepared by 3-hour pulverization had a polyphenol content about 10 times as high as the sample of crystalline honeybee pollen prepared without pulverization in accordance with one embodiment of the present invention.

Polyphenols derived from plants offer excellent functions of promoting the blood circulation; hence, they are widely known to make preventive effects against arteriosclerosis, senile dementia, cerebral infarction, diabetes, cancers, etc. It is also reported that the polyphenols function as a radical scavenger in the prevention of aging and the inhibition of cancers.

In other words, a most effective method of ingesting a large amount of polyphenols is an oral administration of honeybee pollen in the form of the honeybee pollen composition prepared by pulverization according to one embodiment of the present invention rather than a honeybee pollen lump or a pulverized honeybee pollen having a particle size of 1,000 nm or greater.

In conclusion, the honeybee pollen composition according to one embodiment of the present invention can be provided by mixing solidified honeybee pollen with distilled water and an admixture consisting of a dispersant, a preservative, a thickener, an antioxidant, or a neutralizer and then performing pulverization with a particle size of 100 to 500 nm, resulting in an efficient disruption of cell walls of the honeybee pollen and thus advantageously making the honeybee pollen composition into a formulation available for easier ingestion in the body or skin, where the admixture, including a dispersant, a preservative, a thickener, an antioxidant, a neutralizer, etc., is added to the solidified honeybee pollen in the pulverization process to promote the stability, antioxidant effects and polyphenol content of the honeybee pollen composition, thereby acquiring availability of the honeybee pollen composition as a cosmetic material or a pharmaceutical composition. The addition of bacteria and a fermenting agent incurs an efficient disruption of the cell walls of the honeybee pollen without using fermentation, so the honeybee pollen composition can be made into a formulation available for easier ingestion in the body or skin. This simplifies the process of preparing a honeybee pollen composition able to be easily absorbed into the body or skin, and also advantageously prevents, to the maximum, a loss of the active ingredients contained in the honeybee pollen possibly occurring due to the fermentation activated with the aid of bacteria. Further, the honeybee pollen composition according to one embodiment of the present invention includes an admixture of a dispersant, a preservative, a thickener, an antioxidant, a neutralizer, etc. added to the solidified honeybee pollen in the pulverization process, which promotes the stability, antioxidant effects and polyphenol content of the honeybee pollen composition and thereby makes the honeybee pollen composition available as a cosmetic material or a pharmaceutical composition.

The foregoing description of the invention has been presented for purposes of illustration and description. The above-specified examples are all given to illustrate the present invention and not construed to limit the present invention. It is to be apparent to those skilled in the art that the present invention may be readily implemented in various other ways without changing its technical conception or essential features. It is also to be noted that the scope of the present invention includes all the modifications and variations belonging to the principles of the present invention.

INDUSTRIAL AVAILABILITY

The present invention can provide a honeybee pollen composition prepared by mixing solidified honeybee pollen with distilled water and an admixture consisting of a dispersant, a preservative, a thickener, an antioxidant, or a neutralizer and then performing pulverization with a particle size of 100 to 500 nm, resulting in an efficient disruption of cell walls of the honeybee pollen to make the honeybee pollen composition into a formulation available for easier ingestion in the body or skin. As an admixture, including a dispersant, a preservative, a thickener, an antioxidant, a neutralizer, etc., is added to the solidified honeybee pollen in the pulverization process, it promotes the stability, antioxidant effects and polyphenol content of the honeybee pollen composition and thereby acquires availability of the honeybee pollen composition as a cosmetic material or a pharmaceutical composition.

What is claimed is:

1. A honeybee pollen consisting essentially of 3% to 20 wt. % of solidified honeybee pollen, 0.1 to 4 wt. % of carboxymethyl cellulose, 0.1 to 4 wt. % of 1, 2-hexanediol, 1 to 10 wt. % of carbopol, 0.05 to 0.3 wt. % of sodium pyrosulfite, and 0.1 to 1 wt. % of tetraethylammonium.

* * * * *